United States Patent [19]

Lübbers et al.

[11] 4,215,940
[45] * Aug. 5, 1980

[54] OPTODE ARRANGEMENT

[75] Inventors: Dietrich W. Lübbers, Dortmund; Opitz, Norbert, Bochum, both of Fed. Rep. of Germany

[73] Assignee: Max Planck Gesellschaft zur förderung der Wissenschaften E.V., Göttingen, Fed. Rep. of Germany

[*] Notice: The portion of the term of this patent subsequent to Jan. 18, 1994, has been disclaimed.

[21] Appl. No.: 817,109

[22] Filed: Jul. 19, 1977

[30] Foreign Application Priority Data

Jul. 20, 1976 [DE] Fed. Rep. of Germany ....... 2632556

[51] Int. Cl.$^2$ .............................................. G01J 3/46
[52] U.S. Cl. ..................................... 356/402; 356/41; 356/417
[58] Field of Search ................. 356/196, 173, 39, 402, 356/41, 417, 85; 23/330 B, 232 R, 254 R, ; 128/2 G, 2 L, 214 B, DIG. 23; 250/458

[56] References Cited

U.S. PATENT DOCUMENTS 4,003,707  10/1977  Lubbers et al. .................... 23/232 R
4,022,529  5/1977   White ................................ 356/85

Primary Examiner—John K. Corbin
Assistant Examiner—B.W. de los Reyes
Attorney, Agent, or Firm—Michael J. Striker

[57] ABSTRACT

Monochromatic excitation light is passed into an indicator chamber to excite the indicator therein. The side of the indicator chamber in contact with the substance to be analyzed is closed off by a membrane which is permeable to the component of that substance whose concentration is to be determined. The side through which the radiation emitted from the indicator towards the light-measuring unit of the apparatus passes is transmissive for the emitted radiation. The direction of introduction of monochromatic excitation radiation, and the direction in which the radiation emitted from the indicator towards the light-measuring unit, include an angle relative to each other, and are preferably perpendicular. As a result, any spectral reactivity of the substance to be analyzed to the excitation radiation does not have an affect upon the light-measuring unit of the apparatus, and the latter receives light exclusively dependent upon the spectral alteration of the indicator in response to the concentration of the component whose concentration is to be ascertained.

7 Claims, 3 Drawing Figures

OPTODE ARRANGEMENT

BACKGROUND OF THE INVENTION

The invention relates to apparatus for the optical measurement of the concentrations in a substance to be analyzed, for example, oxygen in blood. The type of apparatus in question usually includes a housing containing a monochromator and a light-measuring unit, and an indicator chamber containing an indicator whose spectral response to the light from the monochromator is dependent upon variations in the concentration of the component of interest. The side of the indicator chamber facing the medium to be analyzed is closed off by a membrane which is permeable for the substance of interest. The side of the indicator chamber facing the monochromator is closed off by a layer of material through which the radiation of interest can pass (optode).

With measuring apparatuses of this type, a problem is posed by the fact that the substance to be analyzed may itself respond to the reaction to be measured with a spectral alteration of its own; i.e., the radiation to be measured, namely that attributable to the spectral dependence of the indicator upon the concentration of the component of interest, may have superimposed thereon so-called "background radiation" attributable to the spectral response of the substance to be analyzed itself. Additionally, there may occur at the boundaries of the interior space of the indicator chamber reflection effects which cannot be predicted and compensated for in advance; as a result, the functional relationship between the excitation radiation and the radiation to be measured is no longer determined exclusively by the concentration of the component of interest.

SUMMARY OF THE INVENTION

It is the general object of the invention to provide a novel device of the type in question, but of such a design as to exclude the aforementioned effect of the spectral response of the substance being analyzed, and other such background radiation.

According to one concept of the invention, this is achieved by so designing the apparatus that the light-measuring unit which receives and measures the radiation emitted from the indicator receives that radiation along a radiation path which is oriented at an angle relative to the direction in which the radiation from the monochromator penetrates the indicator.

The advantage of this novel design is that it achieves optical decoupling between the substance to be analyzed and interfering background radiation.

Preferably, the direction in which the radiation to be measured travels from the indicator to the measuring unit is perpendicular to that in which the monochromator radiation travels through the indicator, and preferably, the monochromator radiation travels through the indicator approximately parallel to the membrane plane of the optode.

With this novel arrangement, the monochromator radiation is no longer incident upon the substance to be analyzed, and therefore the latter no longer contributes to the radiation detected by the light-measuring unit of the device.

According to an advantageous concept of the invention, the light from the monochromator is transmitted into the optode by means of a light-conductor element. This further reduces the effect of background radiation, and makes it possible to introduce the monochromator light into the indicator space using inexpensive means.

Advantageously, an intermediate optical coupling element is utilized, between the light-conductor element and the optode per se, to properly direct the light into the indicator space. This makes for high efficiency in the use of the light from the monochromator. This efficiency is further increased, if the optode is made of circular configuration, with the intermediate optical coupling element enclosing or surrounding the optode.

Preferably, the radius of the optode, when the latter is of circular configuration, corresponds to the depth to which the light from the monochromator penetrates into the indicator space. This makes for a very uniform irradiation of the indicator contained within the optode.

If the penetration depth of the monochromator light employed is small, then it is preferred not to make the optode of circular configuration, but instead of elongated configuration. This assures uniform penetration of the indicator by monochromator radiation, and increases the effective measuring surface of the device.

It is also possible to implant generally planar laminar optodes and to excite the entrapped indicator by means of x-ray radiation incident parallel to the general plane of the optode. This makes it possible to obtain physiological undisturbed measurements without the danger of infection, and over very long periods of time.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
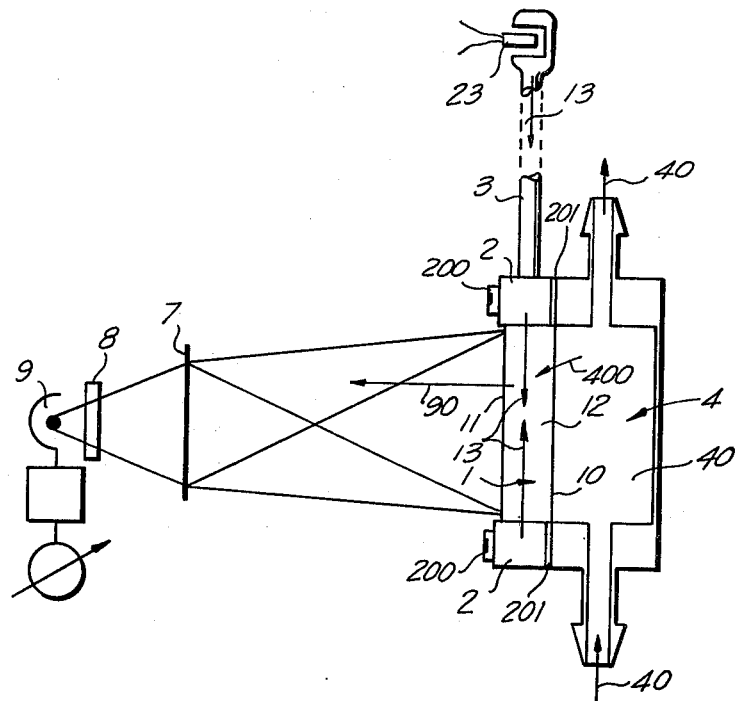
FIG. 1 is a sectional view through an exemplary embodiment of the inventive construction.

An optode 1 is filled with an indicator 12. The side of the optode which faces the substance 40 to be analyzed is closed off by a membrane 10 which is permeable for the component 400 of interest. The side of the optode which faces the light-measuring unit 9 of the device is closed off by a diaphragm through which the radiation of interest can pass, i.e., in order to reach light-measuring unit 9. The substance 40 to be analyzed may, for example, be blood, and the substance 400 of interest oxygen. The indicator 12 could, in that case be, for example, pyrene butyric acid. The membrane 10 could, for example, be Teflon having a thickness of about 12 microns.

The required excitation radiation 13 can be furnished using a light source and a conventional monochromator or, as illustrated here, directly from a monochromatic light source 23. For the substances mentioned by way of example above, the wavelength of the excitation light would be 326 manometers, and the wavelength of the light emitted by the indicator would be 395 nanometers.

The monochromatic excitation radiation 13 is transmitted through a light-conductor element 3 into an intermediate optical coupling element 2, to which the light-conductor element 3 is connected. Coupling element 2 can be made of for example transparent plastic and be of circular configuration. The coupling element 2 directs the monochromatic light 13 received via light-conductor element 3 radially inward into the indicator space, from all around the periphery of the indicator space.

The component 400 of interest, carried within the substance 40 to be analyzed in the chamber 4 for the latter in front of the optode, passes through the permeable membrane 10 into the indicator space of the optode and mixes with the indicator 12. As a result, the indicator 12 undergoes a change of color, or a change in its fluorescence if a fluorescent indicator is being employed. The radiation 90 emitted from the indicator 12 towards the light-measuring unit 9 of the device travels toward the latter perpendicular to the direction in which the monochromator radiation 13 sweeps alongside the membrane 10. Accordingly, this radiation does not include spectral (color) components originating from the monochromator radiation 13; neither does it include any radiation components which would in the prior art have developed in the substance 40 to be analyzed itself. Thus, this novel relationship of the travel paths of the monochromator radiation and of the emitted radiation to be measured by the light-measuring unit 9, in itself, results in a marked reduction in interference components in the signal produced by the light-measuring unit 9. The radiation 90 is projected by an optical system 7 through a filter 8 onto the light-measuring unit 9, and the latter produces a measurement signal in otherwise conventional manner.

Advantageously, the chamber 4 for the substance 40 to be analyzed can be consolidated, along with the optode, into a single structural component, as illustrated, utilizing a plate 201 which is non-transmissive for the monochromator light to prevent spillover into the chamber 4, with the two components being joined by screws or clamps 200.

Figure 3:
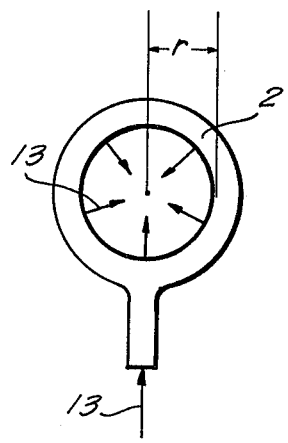
FIG. 3 is a shematic front view of an optode which is of elongated, instead of circular configuration.
Figure 2:
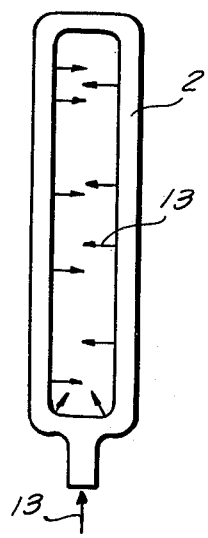
FIG. 2 is a schematic front view of the optode, showing its circular configuration.

Preferably, the radius of the circular optode is equal to the penetration depth of the monochromator light into the indicator space, as shown in FIG. 2. This assures uniform excitation of the indicator 12. If, for example, the penetration depth of the monochromator light employed is low, then to avoid a corresponding reduction in the radius of the circular optode, the optode is preferably of elongated, instead of circular, configuration as shown in FIG. 3, in which case the intermediate optical coupling element 2 of FIG. 1, likewise, would be of elongated instead of circular configuration.

It will be understood that each of the elements described above, or two or more together, may also find a useful application in other types of constructions differing from the types described above.

While the invention has been illustrated and described as embodied in a device for measuring the concentration of a substance passed through a chamber adjoining the optode, it is not intended to be limited to the details shown, since various modifications and structural changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An apparatus for the optical measurement of concentrations of components of a substance to be analyzed, of the type comprised of a source of monochromatic excitation radiation, an indicator chamber containing an indicator into which the monochromatic excitation radiation enters to excite the indicator, the side of the indicator chamber to be contacted by the substance to be analyzed being closed off by a membrane permeable for the component whose concentration is to be determined, the side of the indicator chamber through which radiation emitted from the indicator is to be emitted being transmissive for the emitted radiation, and a light-measuring unit operative for receiving the radiation emitted from the indicator and generating a corresponding signal indicative of the concentration of the component whose concentration is to be determined, the improvement wherein the travel path of the radiation emitted from the indicator to the light-measuring unit extends at an angle relative to the travel path of the monochromatic excitation radiation passing through the indicator chamber.

2. The apparatus defined in claim 1, wherein the two travel paths include with each other an angle of about 90°.

3. The apparatus defined in claim 1, wherein the travel path of the monochromatic excitation radiation passing through the indicator chamber is generally parallel to said membrane.

4. The apparatus defined in claim 3, including a light-conductor element arranged to transmit the excitation energy from the source towards the interior of the indicator chamber.

5. The apparatus defined in claim 4, including an intermediate optical coupling element operative for receiving the radiation tramsmitted by the light-conductor element and directing it inwardly into the interior of the indicator chamber.

6. The apparatus defined in claim 5, wherein the indicator chamber and the optical coupling element are of circular configuration and the indicator chamber has a radius corresponding to the penetration depth of the monochromatic excitation radiation.

7. The apparatus defined in claim 5, wherein the indicator chamber and the optical coupling element are of elongated configuration and the indicator chamber has a transverse breadth corresponding to the penetration depth of the monochromatic excitation radiation.

* * * * *